United States Patent [19]

Albeck et al.

[11] Patent Number: 4,857,325
[45] Date of Patent: Aug. 15, 1989

[54] ANTIOXIDANT COMPOSITIONS AND METHODS

[75] Inventors: Michael Albeck; Shlomo Grossman, both of Ramat-Gan, Israel

[73] Assignee: Bar-Ilan University, Ramat-Gan, Israel

[21] Appl. No.: 846,599

[22] Filed: Mar. 31, 1986

Related U.S. Application Data

[63] Continuation-in-part of Ser. No. 726,540, Apr. 24, 1985, abandoned.

[51] Int. Cl.$^4$ ............................................... A61K 35/78
[52] U.S. Cl. ........................ 424/195.1; 424/DIG. 15; 514/966; 514/969
[58] Field of Search ............... 424/195.1, DIG. 15; 514/966, 969

[56] References Cited

U.S. PATENT DOCUMENTS

| | | | |
|---|---|---|---|
| 2,098,254 | 11/1937 | Mattill et al. | 426/546 |
| 2,282,808 | 5/1942 | Musher | 426/651 |
| 2,382,242 | 8/1945 | Lindow et al. | 426/72 |
| 3,628,971 | 2/1970 | Karchmar | 71/67 |
| 3,883,505 | 5/1976 | Hamuro | 536/124 |
| 3,948,801 | 4/1976 | Braddon et al. | 252/400 A |
| 4,011,206 | 3/1977 | Higginbotham | 530/370 |
| 4,075,406 | 2/1978 | Melaja et al. | 536/124 |
| 4,154,822 | 5/1979 | Polimeni et al. | 514/54 |
| 4,321,360 | 3/1982 | Blount | 536/1 |
| 4,352,746 | 10/1982 | Bracco et al. | 252/398 |
| 4,361,697 | 11/1982 | Dobberstein et al. | 536/128 |
| 4,380,506 | 4/1983 | Kimura et al. | 252/398 |
| 4,499,267 | 2/1985 | Seifoni | 44/51 |
| 4,511,559 | 4/1985 | Szendrei et al. | 514/54 |
| 4,525,306 | 6/1985 | Yajima | 260/428.5 |
| 4,536,496 | 8/1985 | Shimizu et al. | 514/54 |

FOREIGN PATENT DOCUMENTS

| | | |
|---|---|---|
| 2209856 | 9/1973 | Fed. Rep. of Germany. |
| 3207005 | 9/1982 | Fed. Rep. of Germany. |
| 1573315 | 7/1969 | France. |
| 2229388 | 12/1974 | France. |
| 2484836 | 12/1981 | France. |
| WO86/01713 | 3/1986 | World Int. Prop. O.. |

OTHER PUBLICATIONS

Lewis, Medical Rotary, Wiley & Sons, New York, p. 490, 1977.
Patent Abstracts of Japan, unexamined applns. C field, vol. 4, No. 98, Jul. 15, 1980; The Patent Office Japanese Government-p. 134 C 18-Kokai-No. 55-62 005 (Kurorera).
Patent Abstracts of Japan, unexamined applns, C section, vol. 1, No. 27, Mar. 28, 1977; The Patent Office Japanese Government-p. C 3969-Kokai-No. 51-142 514 (A. Fukuda).
Patent Abstracts of Japan, unexamined applns. C section, vol. 1, No. 48, May 11, 1977; The Patent Office Japanese Government-p. 6 C 77-Kokai-No. 52-3 835 (Jefcee Foods).
Patent Abstracts of Japan, unexamined applns. C field, vol. 8, No. 145, Jul. 6, 1984; The Patent Office Japanese Government-p. 57 C 232-Kokai-No. 59-51 763 (Nihon Rikagaku Yakuhin K.K.).
Journal of Food Science, vol. 36, 1971, Chicago, pp. 571, 572-(A. Pinsky et al.)-Totality.
Patent Abstracts of Japan, unexamined applns. C field, vol. 7, No. 122, May 26, 1983; The Patent Office Japanese Government-p. 136 C 168, Kokai-No. 58-42 686 (Hasegawa Koryo K.K.).

*Primary Examiner*—John W. Rollins
*Attorney, Agent, or Firm*—Hedman, Gibson, Costigan & Hoare

[57] ABSTRACT

Antioxidant compositions and methods are disclosed that are prepared by the extraction of natural antioxidants from plant substrates.

61 Claims, 11 Drawing Sheets

ANTIOXIDANT COMPOSITIONS AND METHODS

CROSS REFERENCE TO RELATED APPLICATION

This application is a continuation-in-part of application Ser. No. 726,540, filed Apr. 24, 1985, now abandoned.

BACKGROUND OF THE INVENTION

This invention is concerned with novel compositions and methods that may be used for cosmetics, food preservation or therapeutic purposes.

The use of specific materials to inhibit or prevent oxidative degradation of natural or synthetic materials is well known in the art. Many of the materials that have been utilized for the purpose have been insoluble in water and have been toxic to mammals at both high and low levels. Examples of these materials include BHA (butylated hydroxy anisole) BHT (butylated hydroxy toluene); propyl gallate; and alpha tocopherol. It is known that natural antioxidants are widely distributed in plant tissues. Certain of these antioxidants have been obtained in crude form and have been shown to have an effect on commercial soybean enzyme lipoxygenase (J. Food Science, V. 36 p 571/1971) Japanese patent application No. SHO 58-42686 discloses an alkali-organic solvent extracting process that obtains an antioxidant from white pepper power.

In Medycyna Weterynaryjna 28:430-433, a procedure is disclosed for extracting dried hay or Urtica with boiling distilled water. The product was used within 48 hours of its preparation as an antioxidant for fish meal.

The applicants have discovered that antioxidants that may be obtained by water extraction of plant tissues are absorbed percutaneously through the skin and exert an antioxidant effect on the outer and inner layers of the skin. These effects are advantageously obtained when the antioxidants is applied to the skin as a dispersion in a hydrophillic or hydrophobic base. The cosmetic result from the application of the antioxidant comprises a softening of the skin which is detectable by touching with the fingertips. In addition, it has been found that the peroxide level of the skin is reduced by application of the antioxidant. These compositions may also be utilized for the preservation of food in place of antioxidants such as BHT or BHA.

SUMMARY OF THE INVENTION

The invention comprises compositions and methods which relate to the use of a water soluble antioxidant, derived from plant tissues, which is capable of being absorbed into mammalian skin where it reduces the peroxide level. The antioxidants may be used for food preservation and for therapeutic purposes.

The plant tissues from which these water soluble antioxidants may be obtained are the leaves of *Spinacia oleracea* (spinach); Trifolium (clover); *Medicago sativa* (alfalfa); *Zea mays* (corn); *Nicotiana tabacum* (tobacco); Penicillaria; Allium (onion and garlic); Algae; and the like. Other suitable plants may also be utilized.

Accordingly it is a primary object of this invention to provide a novel antioxidant material.

It is an object of this invention to provide a cosmetic composition and methods which may be used for application to the skin.

It is an object of this invention to provide a composition that may be absorbed through the skin to provide an antioxidant effect.

It is also an object of this invention to provide compositions and methods for therapeutic purposes.

It is also an object to provide compositions and methods for preventing oxidation in foods.

DETAILED DESCRIPTION OF THE INVENTION

Figure 1:
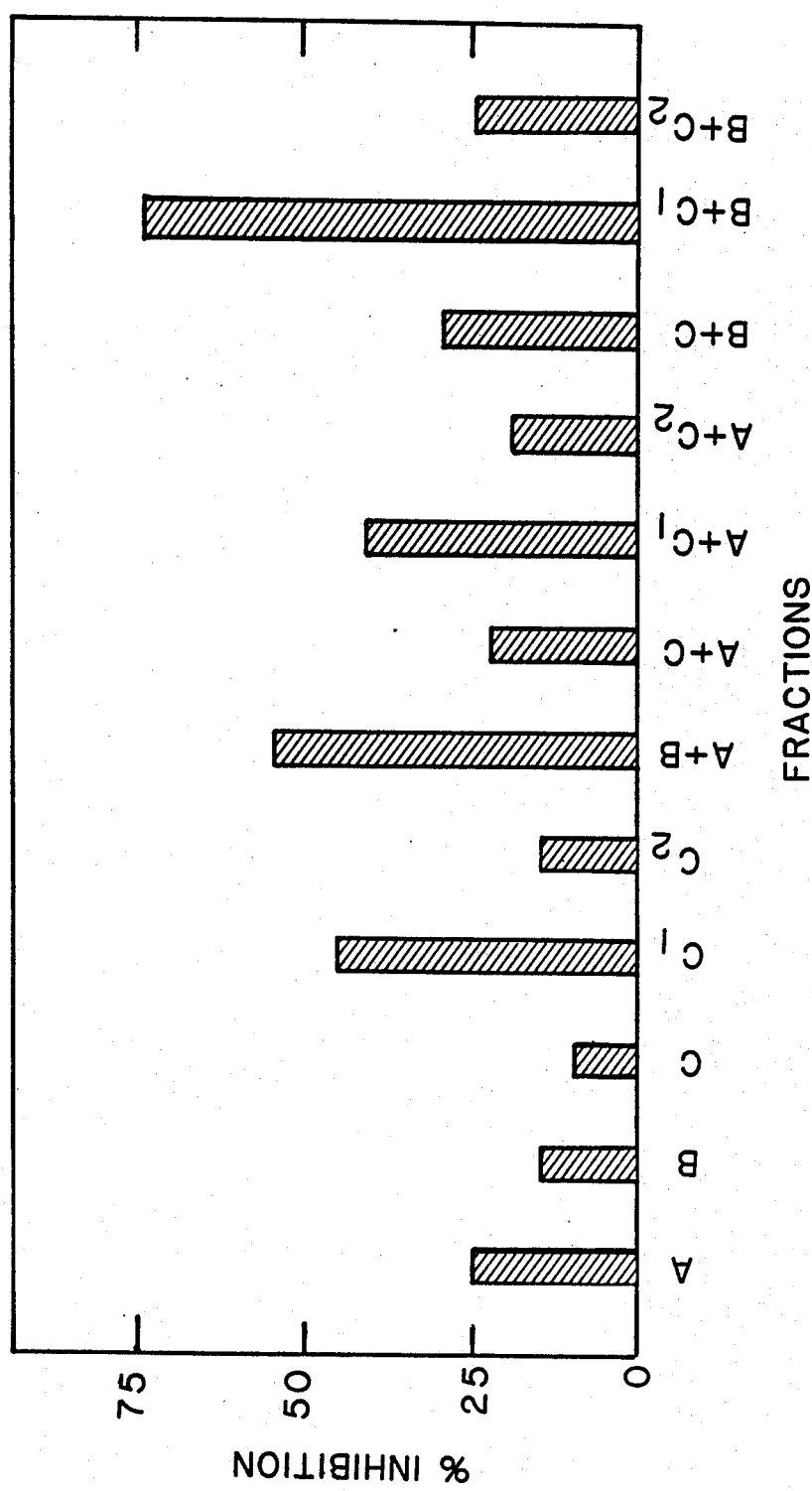
FIG. 1 is a chart which shows the synergistic results of the use of selected antioxidant fractions.

The present invention provides cosmetic compositions for application to the skin. These compositions comprise a cosmetically acceptable carrier and an effective amount of a water soluble extract from plant tissue such as plant leaves and stems which is capable of being absorbed through the skin and lowering the peroxide level of the skin.

The plants that may be utilized as a source of the water soluble extract include the plant tissues of selected speices such as the stems and green leaves selected from the group consisting of Spinacia, Trifolium, Medicago, Zea, Penicillaria, Algae, and Nicotiana. Other plants may be utilized if an aqueous extract of the green leaves provide an antioxidant effect when it is applied to skin. The antioxidant effect is determined by the thiobarbituric acid (TBA) test. This test is described in Food Res. V. 23, P 620 (1958). Generally the level of peroxide in the skin may be determined by assay of a sample of untreated skin which is peeled from a test animal. A preweighed sample of from 10 to 50 mg is homogenized in 0.2M phosphate buffer pH 6.5 and centrifuged. The supernatant is collected and the peroxide level is determined using the TBA test. A sample of skin from the same animal which has been treated according to the invention is also peeled and the peroxide level is determined. A reduction in the peroxide level of about 35% when an antioxidant obtained from a plant is applied as 0.5% w/w dispersion in a petrolatum base is the criteria for determining if a given plant extract is useful according to the present invention.

The cosmetically acceptable carrier may be any liquid or semi-solid type of material that is compatible with the plant extract and non-irritating to the skin.

The water soluble antioxidant may be extracted from the plant material using a plant to water ratio of 0.5:100 to 1.0:5 (w/v as g/ml), preferably 2:1 (w/v as g/ml) after comminution of the plant material. The comminution may be carried out at temperatures of 4° C. to 100° C., preferably at 25° C. using a blender, grinding apparatus or any type of apparatus that will cause fragmentation of the cell walls. The extracted plant material is separated using filtration, centrifugation, decantation, froth flotation or other conventional method used for separating a solid from a liquid.

The crude antioxidant may be used as obtained from the plant either in dilute form or as an aqueous mixture or as a purified extract. Generally it is preferred to separate the aqueous extracting medium from the dissolved antioxidant by evaporation or lyophilization of the liquid portion to provide a dry, water soluble antioxidant. The crude extract may be purified using chromatographic techniques.

Generally, the powder is dissolved in water to form a 10 to 30% w/w solution which is applied to the top of the column and is allowed to move through the column. The various fractions are eluted using water as washing medium and the various fractions are separately collected. The individual fractions may be further purified by a second chromatographic procedure using a packing medium having a smaller pore size.

Sephadex G-25 may be utilized as a chromatographic column separation medium to resolve the crude extract from spinach into a brown fraction (A), a yellow fraction (B) and an orange fraction (C). The orange fraction may be further extracted with water and further separated chromatographically using a Sephadex G-10 column. Sephadex G-25, medium grade, is dextran that has been cross-linked with epichlorohydrin and has a pore size of 50–150-μm. Sephadex G-10 is dextran that has been crosslinked with epichlorohydrin and has a pore size of 40–120 μm. Thin layer chromatography is utilized to separate a yellow fraction from the orange fraction. The Sephadex materials are described in Gel Filtration Theory and Practice, Pharmacia pp 1–64, which is incorporated by reference.

The applicants have isolated several different active antioxidant fractions which may be used separately or in combination. Several of the combined fractions have been shown to have higher activity than the crude fraction.

The relative amounts of the brown, orange and yellow fractions may be varied to give optimum results. Generally any two fractions may be used at weight ratios of 1:99 to 99:1 based on the total weight of the combined fractions. If desired, more than two fractions may be combined at any desired ratio.

For cosmetic use, the total amount of antioxidant that may be used may vary from 0.005 to 5% by weight based on the total weight of the product. A preferred range is from 0.1 to 1%.

The nature of the cosmetic base material is not critical and any suitable cosmetic cream or lotion may be utilized.

The antioxidant may be used in lipstick, face cream, body lotion, moisture creams, burn remedies containing local anesthetics such as 1% benzocaine and the like. The antioxidant has a protective effect against damage to the skin that is induced by UV light having a frequency in the range of 200–340 nm. Therefore, the antioxidant may be applied to the skin, to prevent damage caused by radiation from natural or artificial sources such as the sun, either alone or in combination with sunscreen agents such as PABA.

When foods are preserved with the compositions of the invention an effective amount to prevent oxidation should be used. Generally from 0.001%–1% or more preferably 0.005–0.1% by weight based on the total weight of the foodstuff and antioxidants may be used depending on the foodstuff and the type of oxidative activity that is to be inhibited.

Foods which contain fats or oils such as fatty acid esters or free fatty acids which are saturated or unsaturated may be preserved using the water soluble antioxidant. The fatty acids are well known and are listed in Noller, Textbook of Organic Chemistry, 2nd Ed. pp 108–113 and 138–146 (1958) which is incorporated by reference. Typical foods that contain these fats include soybean oil, corn oil, cottonseed oil, olive oil, butter, margarine, dairy products, ice cream, frozen vegetables, soups, fried foods and the like. In addition, foods which contain compounds that are susceptible to free radical oxidation may be protected with the compounds of the invention. These include foods that contain flavones, carotenoids, tocopherols and the like.

It has also been found that both the crude and purified extracts are stable to high temperature, i.e., boiling water for 30 minutes and have good stability for extended periods at ambient conditions. Toxicity studies have been carried out using both crude and purified fractions and no pathological changes have been detected when the materials have been administered by injection or orally.

The antioxidant has also been shown to be effective in inhibiting tumors such as fibrosarcoma induced by methylcholanthrene and skin cancer such as squamous cell carcinoma which is induced by dimethylbenzoicanthracene, and 4B-phorbol 12-myristate-13-acetate. The compounds may be administered for this purpose at dosages of from 20–500 mg/Kg of body weight orally, rectally or parenterally such as I.P. in mammals such as mice for inhibiting tumors. The invention also includes pharmaceutical compositions that comprise the antioxidants of the invention, together with an inert diluent or carrier. The compound may be administered topically to prevent skin cancers such as melanoma. The compound may be applied in a cosmetically acceptable carrier at a level of 0.005% to 5% by weight.

DESCRIPTION OF THE PREFERRED EMBODIMENTS

Leaves from *Spinacia oleracea* were homogenized with H₂O at 25° C. at a ratio of 2:1 (w/v g/ml) in a Waring blender for 5 min. The resulting homogenate was filtered through cheesecloth and then centrifuged at 15000 X g for 10 min. The supernatant was collected and lyophilized.

Isolation and purification

THe isolation and purification of antioxidant fractions for the crude homogenate preparation was achieved through gel filtration followed by preparative TLC or HPLC. One gram of the lyophilized powder of the crude homogenate was dissolved in 5 ml H₂O and after centrifugation at 20,000 X g for 10 min, the supernatant was applied to a Sephadex G-25 column (40 cm×2.5 cm) equilibrated and eluted with H₂O. Fractions of 5 ml were collected and each was assayed for antioxidant activity. The active fractions (A, B and C) were pooled (fraction A has a brown colour, B-yellow and C-orange) and lyophilized. Fraction C was further purified. The lyophilized material of fraction C was dissolved in H₂O to form a 20% solution (w/v), centrifuged at 20,000 X g for 10 min and the supernatant was chromatographed on a Sephadex G-10 column (40 cm×2.5 cm) equilibrated with H₂O. Fractions $C_1$ and $C_2$ were collected separately and lyophilized as before. Lyophilized fraction $C_1$ was dissolved in a minimum amount of H₂O, applied to 0.2 mm silica gel plates (DC-Karten SIF, Riedel-Dollaen Ag, sleeze-Hanover) and developed in H₂O/ethanol (30/60, v/v). The active fraction was identified by its weak (pale) yellow color and was extracted from the silica gel plate with H₂O and lyophillized.

A further purification was carried out using DEAE cellulose (small size). The fraction identified hereinabove as A was dissolved in water and passed through a 5 cm×1 cm column packed with DEAE cellulose (small size) that had been equilibrated with water that was acidified to a pH of 5-6 with 0.2N HCl. Thereafter the column was washed first with about 50 ml of water and thereafter with 50 ml of aqueous HCl pH 4. The column was eluted with a solution of HCl pH 2.0 and the eluted material was recovered as a powder by vacuum evaporation and was identified as fraction $A_1$. The powder was dissolved in water at a concentration of 20 ug/ml and passed through a high pressure liquid chromatography silica 60 column (250 mm×4 mm) with a 90:10 solution of water:acetonitrile applied at a rate of 0.5 ml/minute. A fraction was obtained that had a retention fraction at 5.4 nanometers (UV absorption).

Figure 7:
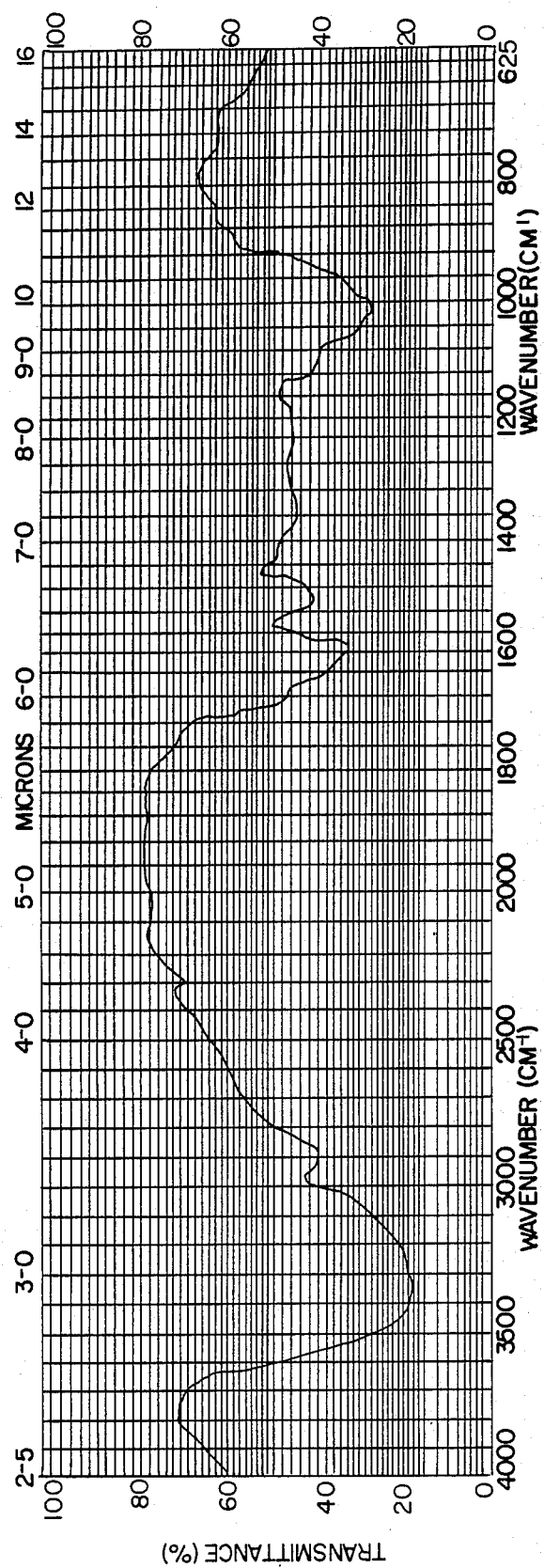
FIG. 7 shows an infrared curve of the antioxidant fraction $A_1$ of the invention, isolated from spinach.

Fraction $A_1$ had the infrared curve of FIG. 7 and an elemental analysis of $C_8H_{10}O_6N_1$; found C 42.02%; H 4.80%; N 6.38%; O 40.09%.

An alternative column packing may be Ecteola, a commecially available condensation product of cellulose with epichlorohydrin and triethanolamine having a capacity of 0.3 to 0.4 meg/g and a particle size of 0.05-0.2 mm.

EXAMPLE 1

From the crude extract of the plant material three antioxidant active fractions (A, B and C) were obtained following the first step of purification. Fraction C was further purified on a column packed with Sephadex G-10 and two other active fractions were obtained by elution with water ($C_1$-dark brown and $C_2$-yellow orange). Fraction $C_1$ was finally purified using HPLC. In studying the antioxidant activity of the crude plant extract and the isolated fractions, both the inhibition of linoleate oxidation by lipoxygenase and the inhibition of auto-oxidation of peroxides were used as criteria for antioxidant activity.

The antioxidant fractions exhibited synergistic activity. The synergism obtained with the natural isolated antioxidants is described in FIG. 1, which depicts the percentage inhibition on lipid oxidation of 1 mg each of single purified antioxidant fractions as well as the analogous percentage inhibition using combinations of 0.5 mg each of two such fractions. By way of example, it may be seen that this synergism increased the potency produced by the compounds from 167% (B+$C_2$) up to 250% (A+B), without increasing the total antioxidant content.

Since lipid peroxidation catalyzed by hemeproteins is a basic deteriorative and pathological reaction, the effectiveness of the isolated fractions to prevent such peroxidation was followed. It was found that the isolated fractions prevent such peroxidation induced by hemoglobin, cytochrome C and myoglobin in a similar way to the inhibition of lipoxygenase induced oxidation.

The purified antioxidant fractions retained their antioxidative activities for months without any loss when kept at room temperature. Moreover, boiling the purified antioxidants for up to 30 minutes did not reduce their antioxidant capacity.

Figure 3:
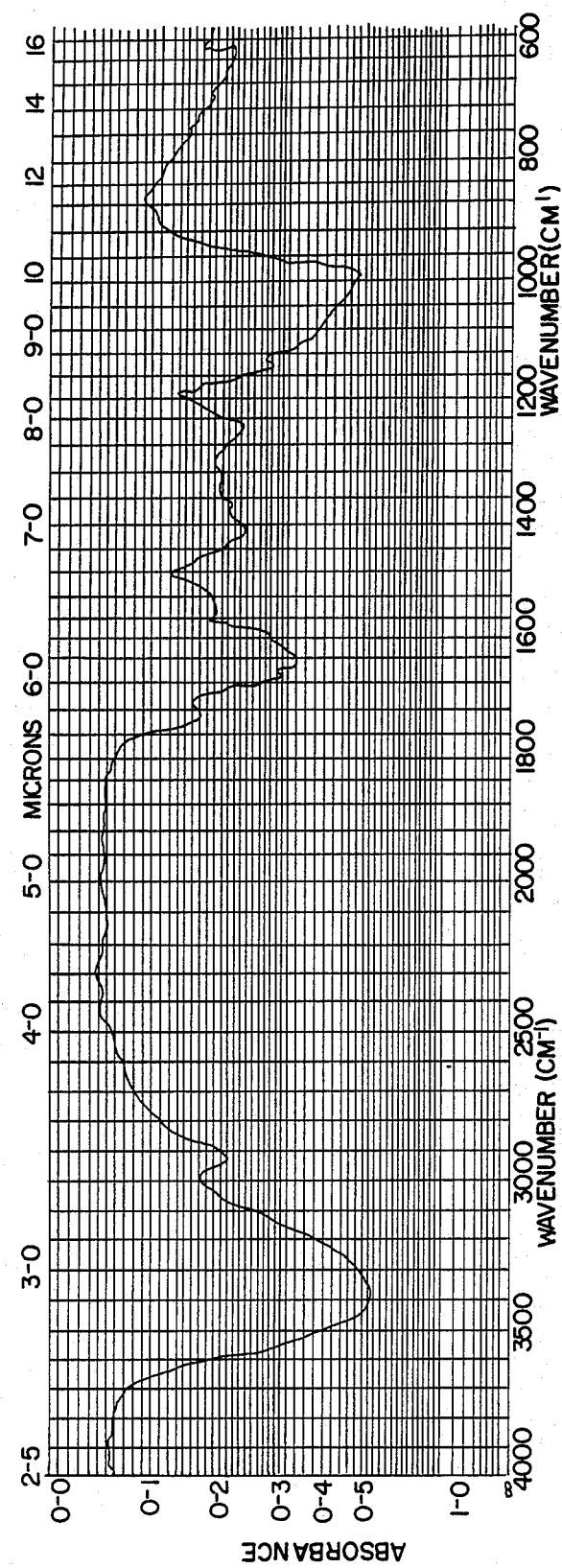
FIG. 3 shows an infrared curve of the antioxidant fraction A of the invention, isolated from spinach.

The following infrared data was obtained from the spinach-derived fractions:

A: (see FIG. 3) broad band at 3400 cm.$^{-1}$, strong bands at 1050 and 1650 cm.$^{-1}$, weak bands at 1250 and 1430 cm.$^{-1}$.

Figure 4:
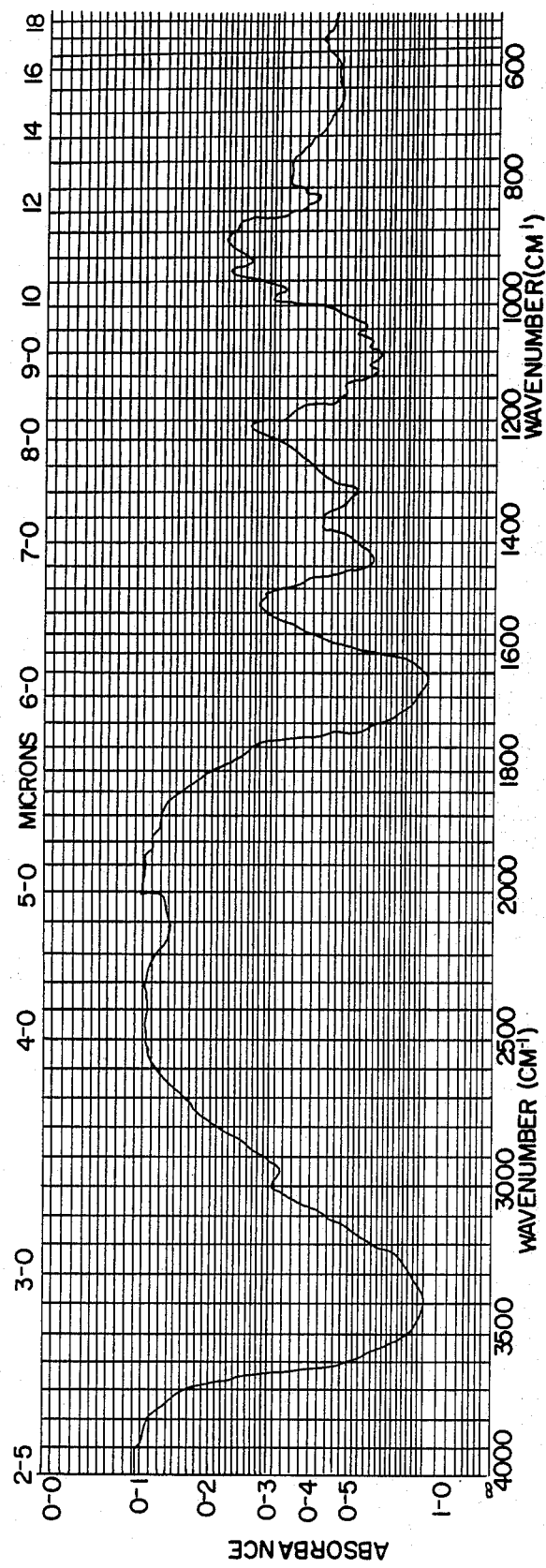
FIG. 4 shows an infrared curve of the antioxidant fraction B of the invention, isolated from spinach.

B: (see FIG. 4) broad bands at 3400, 1640 and 1080 cm.$^{-1}$, additional bands at 1420, 1300 and 810 cm.$^{-1}$.

Figure 5:
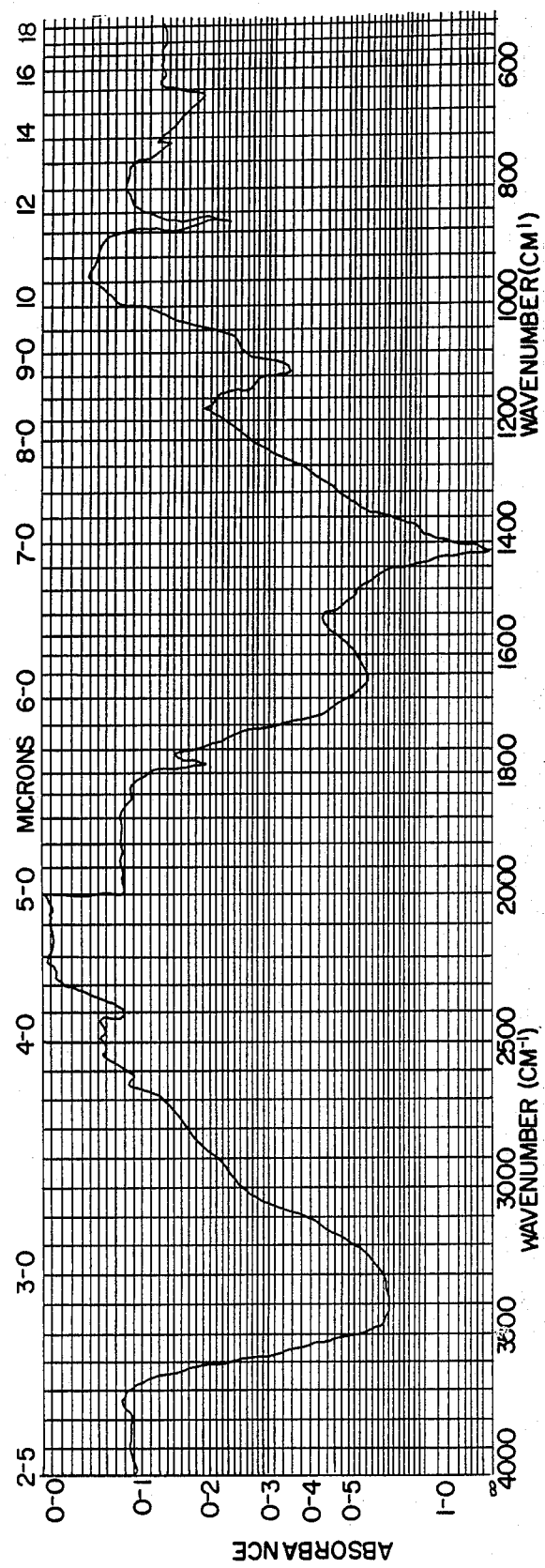
FIG. 5 shows an infrared curve of the antioxidant fraction C of the invention, isolated from spinach.

C: (see FIG. 5) broad bands at 3400 and 1600 cm.$^{-1}$, strong band at 1390 cm.$^{-1}$, additional bands at 1070 and 820 cm.$^{-1}$.

Figure 6:
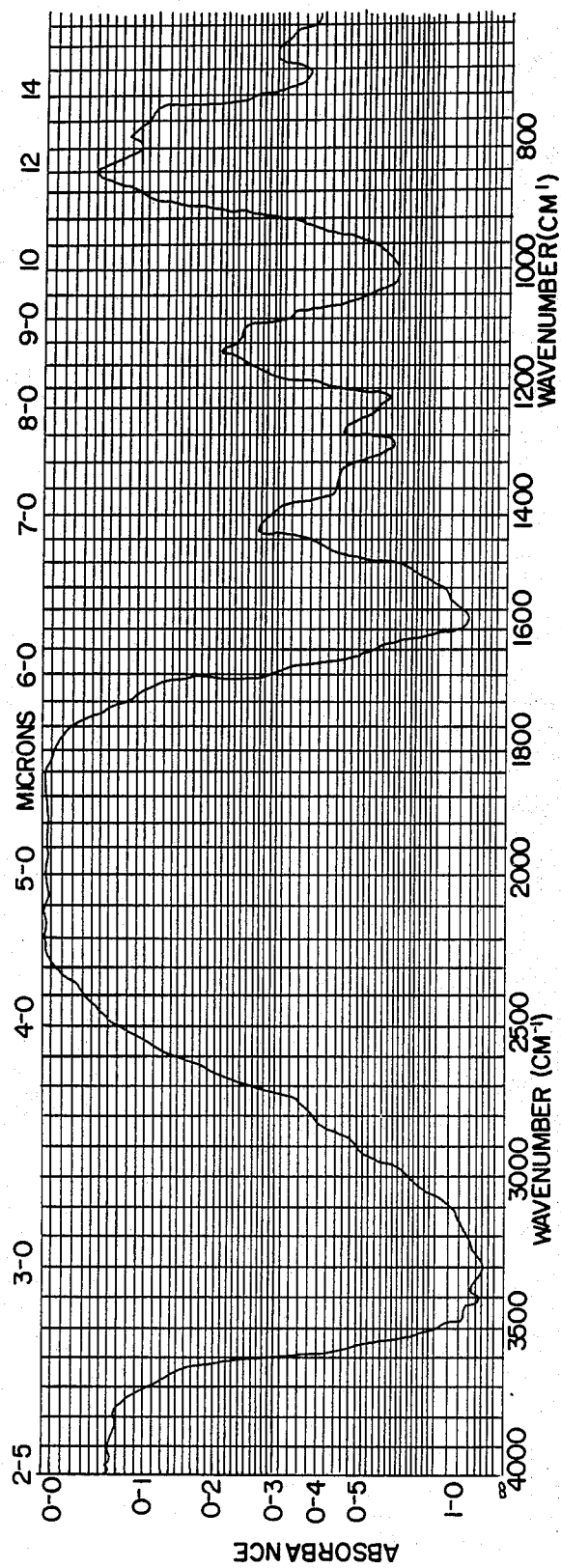
FIG. 6 shows an infrared curve of the antioxidant fraction $C_1$ of the invention, isolated from spinach.

$C_1$: (see FIG. 6) broad band at 3300 cm.$^{-1}$, strong band at 1620 cm.$^{-1}$, additional bands at 1390, 1320, 1080 and 770 cm.$^{-1}$.

$A_1$: (see FIG. 7) broad band at 3300-3400 cm.$^{-1}$, strong band at 1650 cm.$^{-1}$, addl. bands at 1730, 1540, 1250 and 1080 cm.$^{-1}$, weak bands at 2920, 1400 and 1150 cm.$^{-1}$.

EXAMPLE 2

Samples of creams and appropriate controls were applied to mice or rat skin for a fixed period. The application was done once a day. Experiments were terminated by killing the animals, peeling the skin and freezing it in liquid nitrogen. Samples of the frozen skin were homogenized in 0.2M phosphate buffer, pH 6.5. After centrifugation the supernatant was collected and analyzed for the peroxide value using the TBA (Thiobarbituric acid) test as described by Sinnhuber, et al. Food Res. V. 23, p 620 (1958).

Tests with Newborn Rats:

In these experiments newborn rats (hairless) were tested. It is generally considered that the penetration through the skin of newborn rats is better than in adult rats. The advantage of using these rats was that at this early stage they had not yet developed any fur.

TEST NO. 1

In this experiment the control group was treated with Vaseline only, while the test group was treated with Vaseline containing a $C_1$ fraction in Vaseline. A relatively larger amount of the $C_1$ fraction was taken and suspended in the Vaseline. The test was run for 12 days and the results are presented in Table 1.

TABLE 1

| GROUP | TBA O.D.$_{532}$/1 g. tissue | Level of Peroxidation | P value* (n = 3) |
|---|---|---|---|
| Control | 0.295 | 100% | 0.002 |
| +$C_1$ (0.5%) | 0.188 | 64% | 0.002 |

*standard deviation

It is clearly demonstrated that the $C_1$ penetrates the skin of newborn rats and consequently reduces the level of peroxides in the skin. Since peroxides and free radicals involved in their formation and breakdown constitute one of the main routes leading toward aging, the activity of this unique antioxidant can be considered as an anti-aging factor.

TEST NO. 2

In this experiment the antioxidant was dissolved in Oil of Olay obtained in Israel (excellent solubility) and experiments similar to that described in No. 1 was performed. The data are presented in Table 2.

TABLE 2

| GROUP | TBA O.D.$_{532}$/ 1 g. tissue | Level of Peroxidation | P value* (n = 3) |
|---|---|---|---|
| Control (no treatment) | 0.295 | 100% | 0.002 |
| Control (Oil of Olay) | 0.230 | 78% | 0.005 |
| $C_1$ (0.15%) | 0.200 | 68% | 0.011 |
| $C_1$ (1.5%) | 0.191 | 65% | 0.010 |

*standard deviation

As in test No. 1, the Antioxidant significantly reduced the level of peroxides in the skin. It is interesting to point out that in newborn rats, Oil of Olay without the antioxidants also reduced the level of peroxides. This may be attributed to the commercial antioxidants that were present in Oil of Olay that was used. It is possible that in newborn skin, due to its relatively high permeability, small amounts of these antioxidants can also penetrate the skin. However, in adult mice or rats, as will be shown later, Oil of Olay did not reduce that level of peroxides in the skin. On the contrary, in general, a small increase in peroxide level was detected (which perhaps may be attributed to traces of metals in the cream).

EXAMPLE 3

In these experiments adult mice (2 months old) were treated as described in Example 2. The grown mice were shaved before applying the creams to the skin.

In this experiment the antioxidant was dissolved in Oil of Olay. Mice were sacrificed after 21 days. The data are presented in Table 3.

TABLE 3

| GROUP | TBA O.D.$_{532}$/ 1 g. tissue | Level of Peroxidation | P value* (n = 3) |
|---|---|---|---|
| Control (without cream) | 0.338 | 100% | 0.019 |
| Oil of Olay | 0.400 | 118% | 0.026 |
| $C_l$ (0.3%) | 0.240 | 71% | 0.002 |

*standard deviation

It seems that in grown mice the Oil of Olay slightly increases the level of peroxides while addition of the antioxidant at a concentration of 0.3% significantly reduced these peroxides, thus indicating that even with grown mice the antioxidant penetrates the skin. We would like to point out that in similar experiments when we tried the effect of 0.1% BHT, BHA and alpha tocopherol dissolved in Oil of Olay on the level of peroxides in the skin no reduction of the peroxides was observed.

EXAMPLE 4

A new model for studying aging was developed. The new model involves the exposure of adult shaved mice to a UV lamp (sun Lamp 300 W) for a short period. As a result the aging processes as expressed by the level of peroxidation are stimulated and the effect of the natural antioxidant was studied. Using this new technique the optimal antioxidant dose for the inhibition of aging was determined.

In this experiment a crude preparation of antioxidant (and not the final purified antioxidant) was used.

Adult mice were shaved and individuals were exposed to the UV light (Philips HP 3115) (with or without antioxidant) for a short period of 1 minute for two days (two exposures in total). On the third day they were sacrificed and the level of peroxidation in the skin was determined by the TBA (thiobarbituric acid) test.

Controls without exposure to the UV light were also included. Antioxidant was dissolved in Oil of Olay. Data are presented in Table 4.

TABLE 4

EFFECT OF ANTIOXIDANT DOSE ON AGING (EACH GROUP CONTAINED 7 INDIVIDUALS)

| GROUP | TBA O.D.$_{532}$/ 1 g. tissue | Level of Peroxidation | P value* (n = 3) |
|---|---|---|---|
| 1. No radiation | 0.147 | 16.7% | 0.010 |
| 2. Radiation + Oil of Olay | 0.880 | 100% | 0.027 |
| 3. Radiation + 0.3% Antioxidant in Oil of Olay | 0.740 | 84% | 0.006 |
| 4. Radiation + 0.4% Antioxidant in Oil of Olay | 0.680 | 77% | 0.020 |
| 5. Radiation + 0.5% Antioxidant in Oil of Olay | 0.680 | 77% | 0.011 |
| 6. Radiation + 1% Antioxidant in Oil of Olay | 0.700 | 79% | 0.006 |

*standard deviation
The optimal dose of crude antioxidant to be used is 0.3–0.4%.

EXAMPLE 5

Samples of human skin were obtained from a Plastic Surgery Department of a Hospital. These samples were placed in saline solution immediately after their removal from the patients.

The skin samples were exposed to UV rays (Phillips Sun Lamps) for 5 min intervals three successive times with a 5 min rest period between each exposure. The distance between the lamp and the tissue was 12 cm. The skin samples were stored for three days at 4° C. after which time they were peeled and homogenized. 20–30 mg of peeled tissue were assayed for peroxide level using the spectrophotometric TBA test.

The results clearly demonstrate that the peroxide level (aging) of the skin tissue was raised due to exposure to UV rays. Skin treated with the natural antioxidant and exposed to UV rays for the same period of time showed a peroxide level similar to the untreated control.

These results are shown in Table 5.

TABLE 5

| SAMPLE | TBA (O.D.$_{532}$/0.1 gram tissue) | Level of Peroxidation |
|---|---|---|
| Unexposed | 0.050 | 62.5 |
| Exposed | 0.080 | 100 |
| Exposed + Oil of Olay | 0.100 | 125 |
| Exposed + Oil of Olay + (A + B + C) | 0.050 | 62.5 |

The experiments run on human skin indicate the following:
(a) The antioxidant penetrates the skin;
(b) The antioxidant significantly reduces the level of peroxides.

It was noted that when a mixture of fraction A, B and C were used, an effective antioxidant result was observed in the skin.

EXAMPLE 6

The crude extract was tested in vivo for its effect on the immune response system in experimental mice. In these experiments, male Balb-C mice were injected intraperitoneally with 1 mg of the crude extract from *Spinacia oleracea* per 0.2 ml of phosphate buffer solution (PBS) per animal. Animals were sacrificed one, three and seven days after injection and their spleens removed. Spleen cells ($10^7$ cell/ml enriched RPMI) were cultured for 24 hours in the presence of CON A (concavalin-A) 2 µg/ml and the supernatants thus obtained were tested both for IL-2 and (interlukine-2) and CSF (colony stimulating factor). No significant differences were found between controls (i.e., animals receiving no treatment) and experimental animals in their ability to produce IL-2 as well as CSF indicating that the antioxidant has no adverse effect on the immune system. In addition, no pathological findings were observed in injected animals.

Additional testing determined that a single dose of 25 mg/mouse IP may be tolerated and that the $LD_{50}$ is in the range of 1400–1500 mg/kg for mice.

EXAMPLE 7

The $C_1$ fraction was dissolved in (PBS) (50 mg of $C_1$ fraction in 10 ml PBS) 0.2 ml was injected IP into each mouse twice weekly. The $C_1$ fraction was administered orally in an aqueous solution (1 mg/ml) and the mice were allowed to drink the solution from a calibrated bottle to enable measurement of the quantity of the $C_1$ fraction consumed by each individual mouse. Each mouse was injected with 0.6 mg of methylcholantrene, a known inducer of fibrosacoma. Test series A and B were carried out as follows:

| Weeks After Innoculation with MC. Methylcholanthrene | Groups treated with Control Oral Antioxidants | Groups treated with I.P. Antioxidants |
| --- | --- | --- |
| \multicolumn{3}{c}{Tumor Appearance (Animal with tumor/animals in group)} | | |
| TEST A | | |
| 5 weeks | 4/20 | 1/10 | 1/10 |
| 6 weeks | 9/20 | 1/10 | 1/10 |
| 7 weeks | 14/20 | 3/10 | 2/10 |
| 8 weeks | 16/20 | 3/10 | 2/10 |
| 9 weeks | 18/20 | 4/10 | 2/10 |
| TEST B | | |
| 7 weeks | 1/10 | 0/8 | 0/9 |
| 8 weeks | 3/10 | 0/8 | 0/9 |
| 9 weeks | 4/10 | 0/8 | 0/9 |
| 10 weeks | 4/10 | 0/8 | 0/9 |
| 11 weeks | 6/10 | 1/8 | 0/9 |
| 12 weeks | 7/10 | 1/8 | 0/9 |
| 13 weeks | 7/10 | 2/8 | 1/9 |

At week 13 (Test B) (after as many as 25–29 injections) one mouse from each group was sacrificed and observed for gross internal changes (i.e., lymph nodes, spleen, liver, kidney, heart and lung, etc.); no significant changes and no pathological damage was observed. This demonstrated that even a prolonged treatment with the $C_1$ fraction by different routes of administration did not cause any damage to the treated mice.

The in vivo experiments demonstrated that IP or oral administration with $C_1$ is effective in delaying the appearance and reducing the frequency of methylcholanthrene induced tumors.

EXAMPLE 8

Skin tests on human volunteers using a 0.3% w/w dispersion of the crude extract in Oil of Olay have resulted in subjective improvement in the texture of the skin with no adverse effects in any test subjects.

EXAMPLE 9

This example illustrates various compositions that may be used in the practice of the invention.

| Lotion | |
| --- | --- |
| Antioxidant (Example 7) | 1.0 g |
| Base* | 99.0 g |
| | 100.0 g |
| *stearic acid | 1.4 g |
| triethanolmine | 0.6 g |
| glyceryl monostearate | 4.0 g |
| lanolin, hydrous | 1.0 g |
| cetyl alcohol | 0.4 g |
| mineral oil | 2.0 g |
| methylparahydroxybenzoate | 0.1 g |
| distilled water | 90.5 g |
| perfume | g.s. 100.0 g |
| CREAM | |
| antioxidant | 1.0 g |
| cetyl alcohol | 6.4 g |
| stearyl alcohol | 7.4 g |
| isopropyl myristate | 2.0 g |
| sodium lauryl sulfate | 1.4 g |
| white petrolatum | 27.6 g |
| propylene glycol | 9.2 g |
| water, to make | 100.0 g |

EXAMPLE 10

Figure 2:
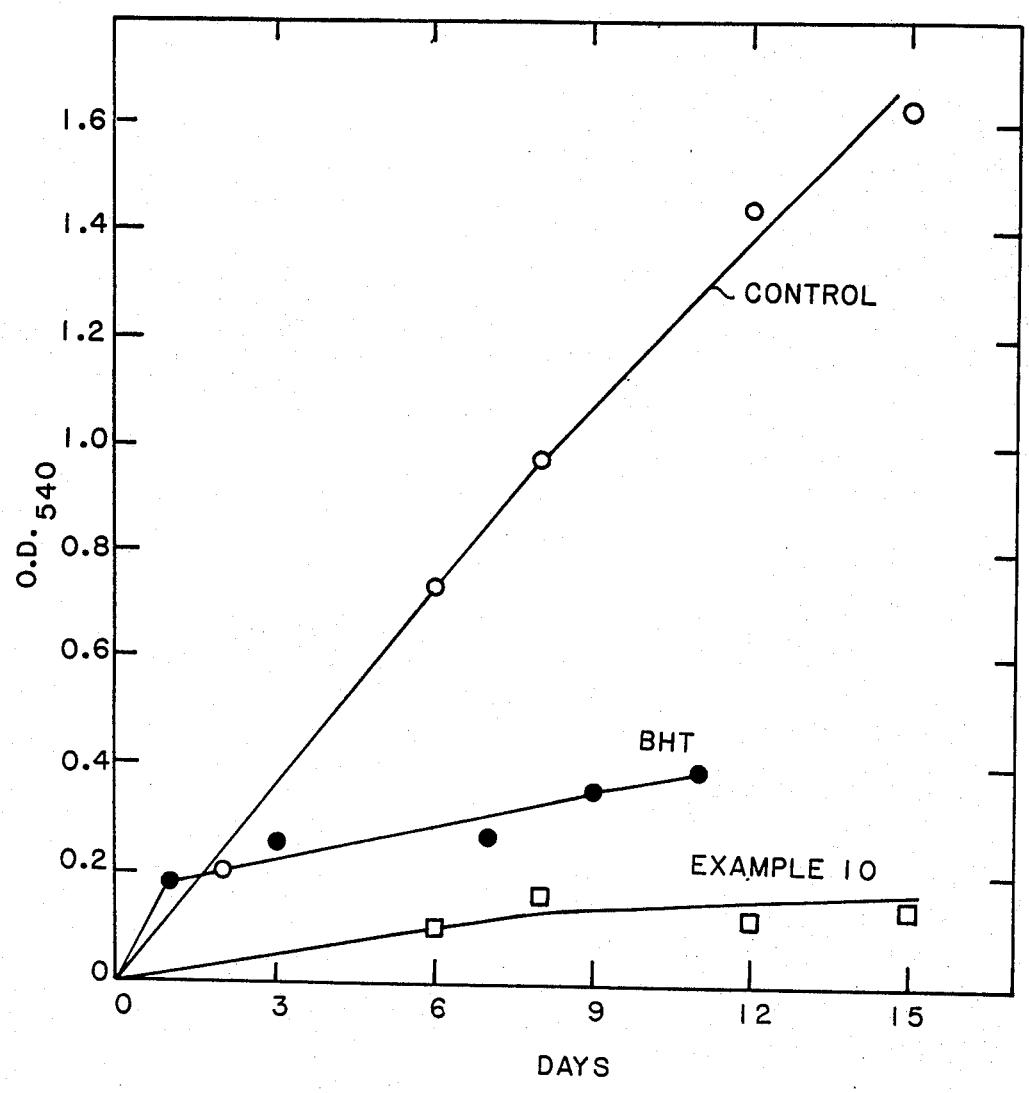
FIG. 2 shows a graphical comparison of the antioxidant effect of the composition of the invention with BHT.

The crude antioxidant (A, B and C) was added to linoleic acid to form a mixture containing 20 ml of $7.5 \times 10^{-3}$ of linoleic acid in 0.2M aqueous sodium phosphate buffer (pH 6.5), containing 0.25% Tween 20 and 1 mg of the crude antioxidant. Controls were run which contained the buffer and Tween 20 but no antioxidant as well as a sample of linoleic acid with 1 mg of BHT and the same dispersant system. The mixture was kept at 30° and the optical density was determined using the ferric thiocyanate method described by Koch et al. in Arch. Biochem. Biophys. Vol. 78, p 165 (1959). The test results on FIG. 2 show that the antioxidant of the invention is more effective than BHT in preventing oxidation of the linoleic acid.

EXAMPLE 11

A similar procedure to that described for spinach, was applied to isolate antioxidant materials from *Trifolium alexandrinum*. The crude extract was separated on Sephadex G-25 to give fractions A, B and C. Fraction A was purified on Ecteola to give fraction $A_1$. Fraction C was resolved on Sephadex G-10 to give fractions $C_1$ and $C_2$. Fraction $C_1$ was further resolved by dissolving in a minimum amount of water, applying to 0.2 mm. silica gel plates and developing in 30:60 v/v $H_2O$-ethanol, to give fractions labelled TLC-1, -2 and -3.

Figure 8:
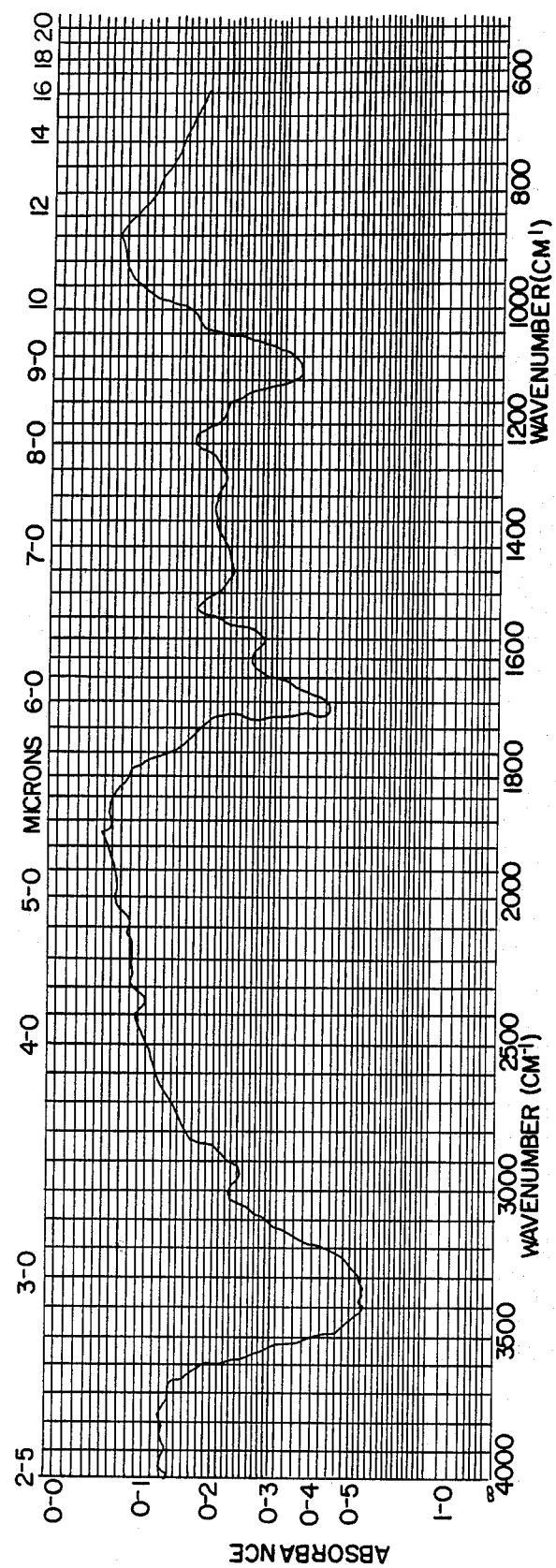
FIG. 8 shows an infrared curve of the antioxidant fraction A of the invention, isolated from clover.

The following infrared data was obtained:
A: (see FIG. 8).

Figure 9:
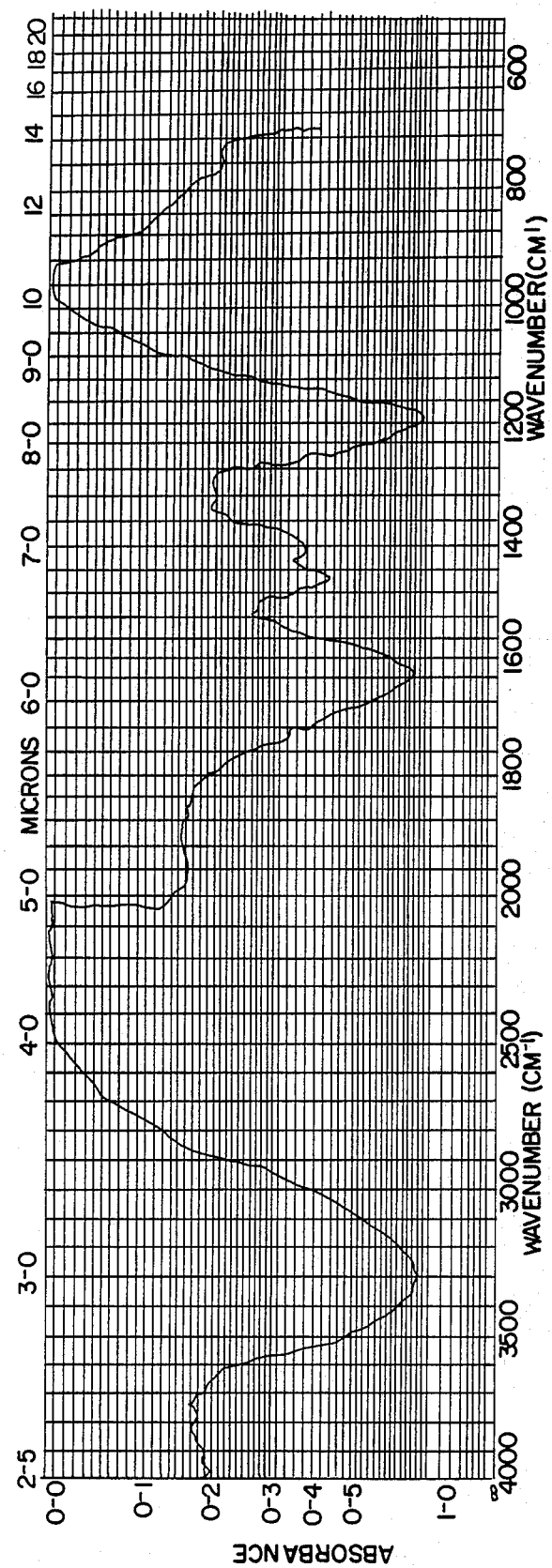
FIG. 9 shows an infrared curve of the antioxidant fraction B of the invention, isolated from clover.

B: (see FIG. 9) strong and broad bands at 3300, 1560 and 1130 cm.$^{-1}$, medium band at 1400 cm.$^{-1}$, weak bands at 1350 and 1430 cm.$^{-1}$.

Figure 10:
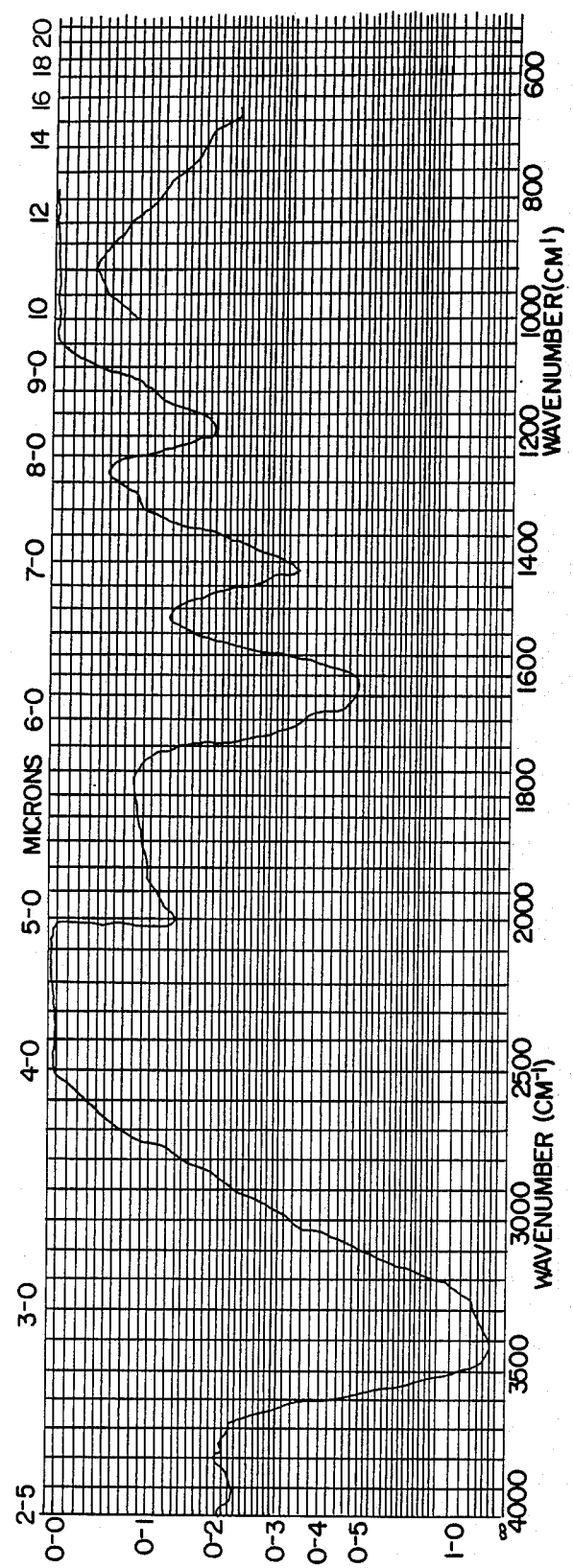
FIG. 10 shows an infrared curve of the antioxidant fraction C of the invention, isolated from clover.

C: (see FIG. 10) broad band at 1370 cm.$^{-1}$, strong bands at 1600, 1380 and 1150 cm.$^{-1}$.

Figure 11:
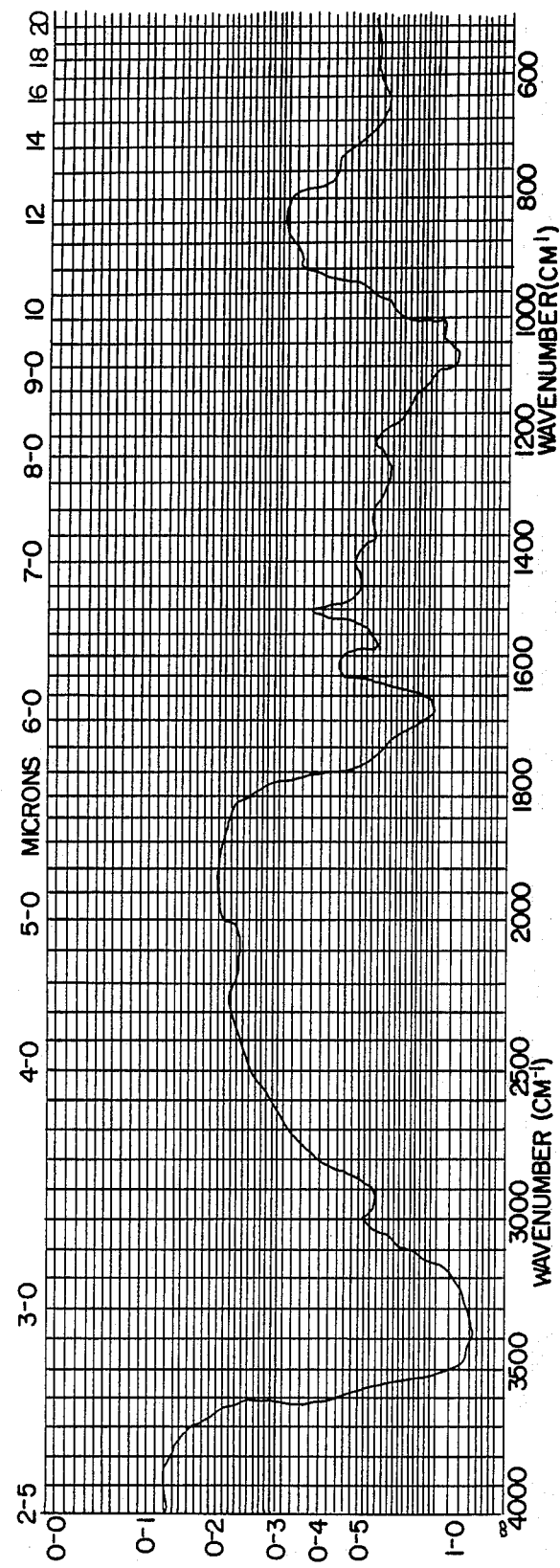
FIG. 11 shows an infrared curve of the antioxidant fraction $A_1$ of the invention, isolated from clover.

A$_1$: (see FIG. 11).

Certain of the foregoing fractions (0.2 mg in each case) derived from clover were tested as antioxidant in a system which contained linoleic acid as substrate and the enzyme lipoxygenase as catalyst. Oxygen absorption was followed using an oxygen monitor according to Grossman and Zakut, in Methods of Biochemical Analysis (D. Glick, Ed.) 25: 303-29 (1979). The following results were obtained.

| Inhibition of Lipid Peroxidation by Antioxidants from Clover | |
|---|---|
| Fraction | % Inhibiton |
| crude extract | 20 |
| A | 9 |
| B | 16 |
| C | 30 |
| TLC-1 | 42 |
| TLC-3 | 46 |

EXAMPLE 12

A number of algae samples were homogenized with distilled water and an extract was prepared according to the technique described above for *Spinacia oleracea*. The crude homogenate was centrifuged and the supernatant was collected and was dried by lyophilization. The dried crude extracts were tested as antioxidants in a system which contained linoleic acid as a substrate and the enzyme lipoxygenase as catalyst. Oxygen absorption was followed using an oxygen monitor according to Grossman and Zakut in Methods of Biochemical Analysis (D. Glick, Ed.) 25, 303-329 (1979). The following results were obtained (2.5 mg of crude extract was used):

| Inhibition of Lipid Peroxidation by Antioxidants from Algae | |
|---|---|
| Algae | % Inhibition |
| Spirulina | 30 |
| Nicractinium | 27 |
| Synichococcus | 30 |
| Navicola | 42 |
| Euglena | 35 |
| Red | 35 |

While the invention has been described above with respect to its presently preferred embodiments, it will be apparent to those skilled in the art that many variations and modifications may be made. The invention is accordingly not to be construed as restricted to the illustrated embodiments, rather its scope will be defined in the claims which follow.

We claim:

1. A composition for application to the skin, said composition comprising a cosmetically acceptable carrier and cosmetically effective amounts of a water soluble extract from plant tissue, said extract and at least two distinct fractions chromatographically separable therefrom being capable of being absorbed through the skin and lowering the peroxide level of the skin, said plant being selected from the group consisting of Spinacia, Trifolium, Medicago, Nicotiana, Penicillaria, Zea, and Allium.

2. A composition as defined in claim 1 wherein the cosmetically acceptable carrier is a hydrophillic cream.

3. A composition as defined in claim 1 wherein the cosmetically acceptable carrier is a hydrophillic lotion.

4. A composition as defined in claim 1 wherein the cosmetically acceptable carrier is a hydrophobic cream.

5. A composition as defined in claim 1 wherein the cosmetically acceptable carrier is a hydrophobic lotion.

6. A composition as defined in claim 1 wherein said water soluble extract from plant tissue is an orange fraction that is chromatographically separated from the supernatant obtained by aqueous extraction of said plant tissue using dextran that was cross-linked with epichlorohydrin and having a pore size of 50-150 μm as the packing for the chromatographic column.

7. A composition as defined in claim 1, wherein said water soluble extract from plant tissue is a brown fraction that is chromatographically separated from the supernatant obtained by aqueous extraction of said plant tissue using dextran that was cross-linked with epichlorohydrin and having a pore size of 40-120 μm as the packing for the chromatographic column.

8. A composition as defined in claim 1, wherein said water soluble extract from plant tissue is a yellow fraction that is chromatographically separated from the supernatant obtained by aqueous extraction of said plant tissue being dextran that has been cross-linked with epichlorohydrin and having a pore size of 50-150 μm as the packing for the chromatographic column.

9. A composition as defined in claim 1, wherein said water soluble extract comprises a mixture of two or more of the orange, yellow and brown fractions that are chromatographically separated from the supernatant obtained by aqueous extraction of said plant tissue being dextran that has been cross-linked with epichlorohydrin and having a pore size of 40-120 μm as the packing for the chromatographic column.

10. A method of cosmetically enhancing the texture of the skin which comprises applying to the skin a composition comprising a cosmetically acceptable carrier and cosmetically effective amounts of a water soluble extract from plant tissue, said extract and at least two distinct fractions chromatographically separable therefrom being capable of being absorbed through the skin and lowering the peroxide level of the skin and said plant being selected from the group consisting of Spinacia, Trifolium, Medicago, Nicotiana, Penicillaria, Zea, and Allium.

11. A method of cosmetically enhancing the texture of the skin which comprises applying to the skin the composition of claim 2.

12. A method of cosmetically enhancing the texture of the skin which comprises applying to the skin the composition of claim 3.

13. A method of cosmetically enhancing the texture of the skin which comprises applying to the skin the composition of claim 4.

14. A method of cosmetically enhancing the texture of the skin which comprises applying to the skin the composition of claim 5.

15. A method of cosmetically enhancing the texture of the skin which comprises applying to the skin the composition of claim 6.

16. A method of cosmetically enhancing the texture of the skin which comprises applying to the skin the composition of claim 7.

17. A method of cosmetically enhancing the texture of the skin which comprises applying to the skin the composition of claim 8.

18. A method of cosmetically enhancing the texture of the skin which comprises applying to the skin the composition of claim 9.

19. An antioxidant composition of matter having the infrared curve of FIG. 7.

20. An antioxidant composition of matter having the infrared curve of FIG. 3.

21. An antioxidant composition of matter having the infrared curve of FIG. 4.

22. An antioxidant composition of matter having the infrared curve of FIG. 5.

23. An antioxidant composition of matter having the infrared curve of FIG. 6.

24. An antioxidant material selected from the group consisting of a water soluble extract prepared from plant tissue and distinct fractions separable from said extract by chromatography, said material and at least two of said fractions being capable of being absorbed through the skin and lowering the peroxide level of the skin and said plant being selected from the group consisting of Spinacia, Trifolium, Medicago, Nicotiana, Zea, Penicillaria and Allium.

25. An antioxidant material according to claim 24, wherein the plant tissue is constituted by at least one member selected from the group consisting of fresh leaves and stems.

26. An antioxidant material according to claim 24, wherein said extract is chromatographically separable on dextran which has been cross-linked with epichlorohydrin and has a pore size of 50-150 $\mu$m, into fractions which are colored brown(A), yellow(B) and orange(C), and of which fraction A is chromatographically purifiable on a substance selected from the group consisting of (i) a condensation product of cellulose with epichlorohydrin and triethanolamine having a capacity of 0.3 to 0.4 meq./g. and a particle size 0.05-0.2 mm., and (ii) dextran which has been cross-linked with epichlorohydrin and has a pore size of 40-120 $\mu$m, to give a fraction (A$_1$) having an infrared spectrum with substantially the following features, namely, broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$, and of which fractions, fraction C is chromatographically separable on dextran which has been cross-linked with epichlorohydrin and has a pore size of 40-120 $\mu$m, into fractions colored dark brown(C$_1$) and yellow orange(C$_2$).

27. An antioxidant material which comprises at least one substance selected from the group consisting of fractions A, A$_1$, B, C$_1$ and C$_2$, as defined in claim 26.

28. An antioxidant material which comprises an antioxidatively synergistic combination of fractions A, A$_1$, B, C$_1$ and C$_2$, as defined in claim 26.

29. An antioxidant material, which is obtainable by extraction of plant tissue with water and subsequent fractionation by chromatographic methods, and having an infra-red spectrum with the features of a member selected from the group consisting of (i), (ii), (iii), (iv), (v), (vi) and (vii), namely:

(i) broad band at 3400 cm.$^{-1}$, strong bands at 1050 and 1650 cm.$^{-1}$ weak bands at 1250 and 1430 cm.$^{-1}$;

(ii) broad bands at 3400, 1640 and 1080 cm.$^{-1}$ additional bands at 1420, 1300 and 810 cm.$^{-1}$;

(iii) broad band at 3300 cm.$^{-1}$, strong band at 1390 cm.$^{-1}$, additional bands at 1070 and 820 cm.$^{-1}$ (iv) broad band at 3300 cm.$^{-1}$, strong band at 1620 cm.$^{-1}$ additional bands at 1390, 1320, 1080 and 770 cm.$^{-1}$;

(v) broad band at 3300-3400 cm.$^{-1}$, strong band at 1650 cm.$^{-1}$, addl. bands at 1730, 1540, 1250 and 1080 cm.$^{-1}$, weak bands at 2920, 1400 and 1150 cm.$^{-1}$;

(vi) broad band at 3430 cm.$^{-1}$, strong bands at 1600, 1380 and 1150 cm.$^{-1}$.

(vii) broad band at 3430 cm.$^{-1}$, strong bands at 1600, 1380 and 1150 cm.$^{-1}$.

30. A process according to claim 24, wherein said extracting step is carried out after a preliminary step of comminuting said plant tissue.

31. A process according to claim 24, wherein said preliminary step is effected at a temperature within the range of from about 4° to about 100° C.

32. A process according to claim 31, wherein said temperature is about 25° C.

33. A process according to claim 24, wherein said fractionation comprises chromatographically separating said extract on dextran which has been cross-linked with epichlorohydrin and has a pore size of 50-150 $\mu$m, into fractions which are colored brown(A), yellow(B) and orange(C), and optionally effecting at least one of the following chromatographic purifications on said fractions, namely:

chromatographically purifying fraction A on a condensation product of cellulose with epichlorohydrin and triethanolamine having a capacity of 0.3 to 0.4 meq./g. and a particle size 0.05-0.2 m.m., or on dextran which has been cross-linked with epichlorohydrin and has a pore size of 40-120 $\mu$m, to give a fraction(A$_1$) having an infrared spectrum with substantially the following features, namely, broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;

chromatographically separating fraction C on dextran which has been cross-linked with epichlorohydrin and has a pore size of 40-120 $\mu$m, into fractions colored dark brown(C$_1$) and yellow orange(C$_2$).

34. A composition of matter for therapeutic or cosmetic use, which comprises a stable antioxidant material as defined in claim 24, together with an inert diluent or carrier.

35. A composition according to claim 34, wherein said composition contains from about 0.005 to about 5% by weight of said antioxidant material, based upon the total weight of the composition.

36. A composition according to claim 34, wherein said composition is in the form of a member selected from the group consisting of a hydrophilic cream, a hydrophilic lotion, a hydrophobic cream and a hydrophobic lotion.

37. A composition according to claim 36, wherein the inert diluent or carrier is adapted for oral, rectal or parenteral administration.

38. A method for cosmetically enhancing the texture of the skin, which method comprises applying to the skin a composition which comprises a antioxidant material as defined in claim 24, together with an inert diluent or carrier which is adapted for application to the skin.

39. A method for cosmetically enhancing the texture of the skin, which method comprises applying to the skin a composition which comprises a antioxidant material as defined in claim 25, together with an inert diluent or carrier which is adapted for application to the skin.

40. A method for cosmetically enhancing the texture of the skin, which method comprises applying to the skin a composition which comprises a antioxidant material as defined in claim 26 together with an inert diluent or carrier which is adapted for application to the skin.

41. A method for cosmetically enhancing the texture of the skin, which method comprises applying to the skin a composition which comprises a antioxidant material as defined in claim 27, together with an inert diluent or carrier which is adapted for application to the skin.

42. A method for cosmetically enhancing the texture of the skin, which method comprises applying to the skin a composition which comprises a antioxidant material as defined in claim 28, together with an inert diluent or carrier which is adapted for application to the skin.

43. A method for lowering the peroxide level of the skin which comprises applying to the skin an effective amount of the composition according to claim 34.

44. A composition for providing an antioxidant effect to the skin, said composition comprising a cosmetically acceptable carrier and an cosmetically effective amount of a water soluble extract from the fresh leaves and stems of a plant selected from the group consisting of Spinacia, Trifolium, Medicago, Nicotiana, Zea, Penicillaria and Allium, wherein said water soluble extract has been chromatographically separated from the supernatant obtained by aqueous extraction of said fresh leaves or stems.

45. A composition as defined in claim 44, wherein the water soluble extract is obtained by a process which consists essentially of aqueous extraction of said stems and leaves by an extractant that consists essentially of water.

46. A composition as defined in claim 45, wherein the process is carried out at a temperature of from 4°–100° C.

47. A composition as defined in claim 46, wherein the process is carried out at the ambient temperature.

48. A composition as defined in claim 45, wherein said water soluble extract from plant tissue is a brown fraction that has been chromatographically separated from the supernatant obtained by aqueous extraction of said plant tissue using dextran that was cross-linked with epichlorohydrin and having a pore size of 40–120 $\mu$m as the packing for the chromatographic column.

49. A composition as defined in claim 45, wherein said water soluble extract from plant tissue is a yellow fraction that has been chromatographically separated from the supernatant obtained by aqueous extraction of said plant tissue using dextran that has been cross-linked with epichlorohydrin and having a pore size of 50–150 $\mu$m as the packing for the chromatographic column.

50. A composition as defined in claim 45, wherein said water soluble extract comprises a mixture of two or more of the orange, yellow and brown fractions that has been chromatographically separated from the supernatant obtained by aqueous extraction of said plant tissue using dextran that has been cross-linked with epichlorohydrin and having a pore size of 40–120 $\mu$m as the packing for the chromatographic column.

51. A composition as defined in claim 45, wherein said plant is selected from Spinacia.

52. A composition as defined in claim 45, wherein said plant is selected from Trifollium.

53. A composition as defined in claim 45, wherein said plant is selected from Medicago.

54. A composition as defined in claim 45, wherein said plant is selected from Nicotiana.

55. A composition as defined in claim 48, wherein said plant material is selected from Allium.

56. A composition as defined in claim 48, wherein said plant material is selected from Penicillaria.

57. A method of cosmetically enhancing the texture of the skin, which comprises applying to the skin a composition as defined in claim 44.

58. A method of cosmetically enhancing the texture of the skin, which comprises applying to the skin a composition as defined in claim 45.

59. A method of lowering the peroxide level of the skin, which comprises applying to the skin an amount of the composition of claim 44, which will lower the peroxide content of the skin.

60. A method of lowering the peroxide level of the skin, which comprises applying to the skin an amount of the composition of claim 45, which will lower the peroxide content of the skin.

61. A composition as defined in claim 45, wherein said antioxidant is stable to boiling water for 30 minutes.

* * * * *